United States Patent
Vermeulen et al.

(10) Patent No.: US 7,519,160 B2
(45) Date of Patent: Apr. 14, 2009

(54) SCANNING X-RAY APPARATUS (75) Inventors: Andries Gerhardus Johannes Vermeulen, Moreletapark (ZA); Johannes Hermanus Potgieter, Midrand (ZA); Paul Van Looy, Randburg (ZA)

(73) Assignee: Lodox Systems (Proprietary) Limited, Sandton (ZA)

( * ) Notice: Subject to any disclaimer, the term of this patent is extended or adjusted under 35 U.S.C. 154(b) by 0 days.

(21) Appl. No.: 10/591,702

(22) PCT Filed: Mar. 3, 2005

(86) PCT No.: PCT/IB2005/000542

§ 371 (c)(1), (2), (4) Date: Apr. 16, 2007

(87) PCT Pub. No.: WO2005/084550

PCT Pub. Date: Sep. 15, 2005

(65) Prior Publication Data

US 2007/0195935 A1 Aug. 23, 2007

(30) Foreign Application Priority Data

Mar. 4, 2004 (ZA) .................................. 2004/1782

(51) Int. Cl.
*G21K 1/02* (2006.01)
*G21K 1/00* (2006.01)

(52) U.S. Cl. .................... 378/147; 378/150; 378/145

(58) Field of Classification Search ............... 378/62, 378/98.8, 145–153, 193, 196–198
See application file for complete search history.

(56) References Cited

U.S. PATENT DOCUMENTS

| 5,164,976 | A | * | 11/1992 | Scheid et al. ............... 378/146 |
| 5,206,765 | A | | 4/1993 | Träger |
| 5,224,136 | A | | 6/1993 | Toth et al. |
| 5,396,534 | A | * | 3/1995 | Thomas ..................... 378/160 |
| 6,055,295 | A | * | 4/2000 | Murthy et al. ............. 378/151 |
| 6,106,152 | A | * | 8/2000 | Thunberg ................... 378/205 |
| 6,478,462 | B2 | * | 11/2002 | Polkus et al. ............... 378/207 |
| 6,921,200 | B1 | | 7/2005 | Booysen et al. |
| 2001/0005409 | A1 | | 6/2001 | Gohno et al. |
| 2002/0196899 | A1 | | 12/2002 | Karellas |
| 2003/0081821 | A1 | | 5/2003 | Mertelmeier et al. |
| 2003/0112924 | A1 | | 6/2003 | Seufert |
| 2003/0128801 | A1 | | 7/2003 | Eisenberg et al. |

FOREIGN PATENT DOCUMENTS

WO  WO 03/055393  7/2003

\* cited by examiner

*Primary Examiner*—Irakli Kiknadze
(74) *Attorney, Agent, or Firm*—Buchanan Ingersoll & Rooney PC (57) ABSTRACT

Linear scanning x-ray apparatus generates a collimated fan beam which is moved together with a detector relative to a subject to generate a composite x-ray image of the subject. An adjustable collimator varies the width of the imaging beam in the scan direction. A control system responds to adjustment of the collimator to combine output signals of groups of two or more pixels in the detector, in order to optimize the contrast resolution of the image signals for a given spatial resolution. The invention provides a collimator for use in the apparatus.

15 Claims, 5 Drawing Sheets

SCANNING X-RAY APPARATUS

BACKGROUND OF THE INVENTION

This invention relates to imaging apparatus of the kind comprising a radiation source and a detector which are moveable relative to a subject; a collimator for adjusting the effective width of an imaging beam generated by such apparatus; and a method of operating such apparatus.

Imaging apparatus which utilizes an x-ray source and an associated detector is known, in which the x-ray source and detector are moved relative to a subject in a scanning process, in order to generate a composite x-ray image of the subject. Apparatus of this kind is described in International patent application no. WO 00/53093, for example. In the apparatus described in the abovementioned patent application, an x-ray source is mounted on one end of a C-shaped arm and emits a low-dose collimated fan beam of x-rays. Mounted on the opposite end of the C-arm is an x-ray detector unit, comprising scintillator arrays optically linked to charge coupled devices (CCDs). An image is obtained by linearly moving the C-arm over the length of a subject or patient with the x-ray source active, while continually reading the output of the detectors. The principle of operation of such apparatus is commonly referred to as linear scanning.

In apparatus of this kind, a number of possibly conflicting parameters affect the characteristics of the final image. Firstly, in order to increase the resolution of a linear slit scanner, it is usually desirable to reduce the width of the imaging beam in the scanning direction as far as possible. This requires the use of a beam limiting device, which is wasteful of x-ray energy and requires a relatively higher x-ray generation capacity than a comparable full field system. A second consideration relates to a trade-off between spatial resolution and contrast resolution. In the example apparatus referred to above, the output of individual pixels in the CCDs can be combined or "binned", which lowers the spatial resolution of the resultant image but enhances the signal to noise ratio and thus the contrast resolution of the image. Depending on the nature of the image required, contrast resolution may be a more important image characteristic than spatial resolution in certain cases.

In the light of the above considerations and others, it is an object of the invention to provide imaging apparatus, and a method of operating such apparatus, which enable optimization of a selected characteristic of the image signals generated.

SUMMARY OF THE INVENTION

According to a first aspect of the invention there is provided imaging apparatus comprising:
 a radiation source for generating an imaging beam;
 a detector responsive to the imaging beam to generate image signals and comprising an array of pixels arranged in rows and columns, each pixel being responsive to incident radiation to generate an output signal;
 a drive arranged to move the radiation source and the detector relative to a subject in a scanning direction;
 an adjustable collimator arranged to vary the width of the imaging beam in the scanning direction; and
 a control system responsive to adjustment of the collimator to combine output signals of groups of two or more pixels in the detector, thereby to optimize a selected characteristic of the image signals.

Preferably, the control system is arranged to combine the output signals of groups comprising greater numbers of pixels as the collimator is adjusted to increase the width of the imaging beam in the scanning direction, thereby to increase the contrast resolution of the image signals for a given spatial resolution.

Each group of pixels preferably defines a super pixel comprising an array of fundamental pixels, the number of fundamental pixels in the array being selected according to a corresponding collimator setting.

The relationship between collimator settings and the number of fundamental pixels in an array defining a super pixel may be stored in a lookup table and related to respective ones of a plurality of different x-ray procedures.

The control system may be arranged to measure the signal level of the detected imaging beam and to adjust the collimator slit width to maintain the detected signal level at or close to a desired setpoint.

According to a second aspect of the invention there is provided a method of operating imaging apparatus of the kind having a radiation source and an associated detector which are moveable relative to a subject, the method comprising:
 generating an imaging beam from the radiation source;
 moving the radiation source and the detector relative to a subject in a scanning direction to generate output signals from each of a plurality of pixels of the detector;
 adjusting a collimator to vary the width of the imaging beam in the scanning direction;
 detecting the setting of the collimator; and
 combining the output signals of groups of two or more pixels according to the setting of the collimator, thereby to optimize a selected characteristic of the image signals.

The method may comprise combining the output signals of groups comprising greater numbers of pixels as the collimator is adjusted to increase the width of the imaging beam in the scanning direction, thereby to increase the contrast resolution of the image signals for a given spatial resolution.

Preferably, each group of pixels defines a super pixel comprising an array of fundamental pixels, the number of fundamental pixels in the array being selected according to a corresponding collimator setting.

The relationship between collimator settings and the number of fundamental pixels in an array defining a super pixel may be stored in a lookup table and related to respective ones of a plurality of different x-ray procedures.

According to a further aspect of the invention there is provided a collimator for adjusting the effective width of an imaging beam generated by a radiation source, the collimator comprising:
 first and second shutter elements arranged side by side to define a slit through which radiation emitted by the source can pass;
 a drive arranged to move the shutter elements in a direction parallel to the slit; and
 a guide mechanism comprising first and second tapered surfaces arranged to cooperate with respective tapered surfaces on the first and second shutter elements, so that operation of the drive varies the width of the slit.

This arrangement ensures that both the shutter elements move co-centrically with respect to the centre line that passes through the gap between then, which is necessary in order to obtain the optimum umbra to penumbra ratio of the x-ray beam on the detector.

Each shutter element preferably comprises a strip of radiation-opaque material and a supporting body defining the respective tapered surface.

The drive may be a rotary drive such as a motor and reduction drive with a ball screw or similar mechanism arranged to impart linear motion to the shutter elements, or a linear drive such as a solenoid, for example.

Preferably, the shutter elements are biased towards a position in which the width of the slit is a minimum.

DESCRIPTION OF AN EMBODIMENT

Figure 1:
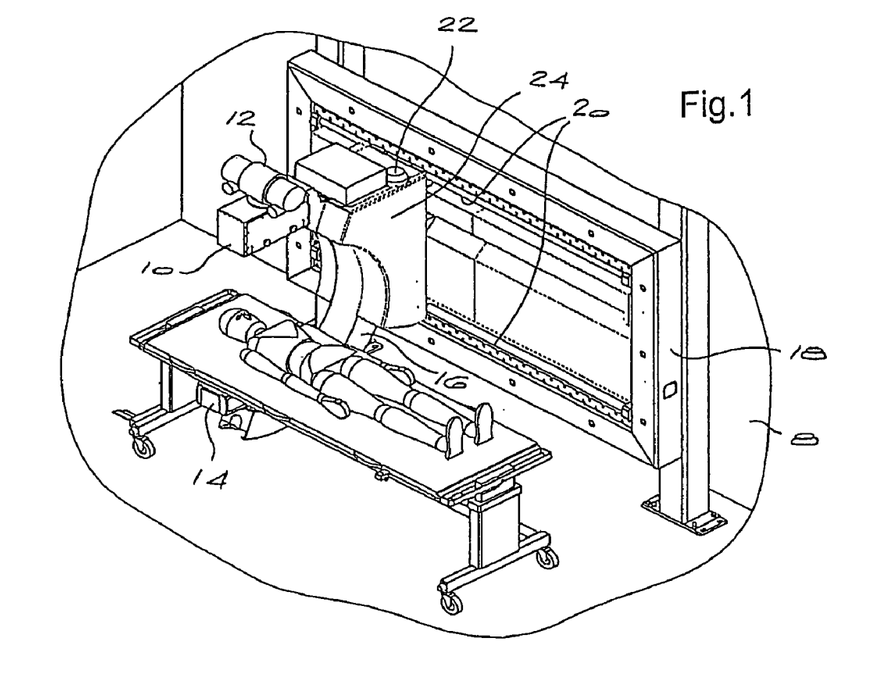
FIG. 1 is a pictorial view of imaging apparatus according to the invention.
Figure 2:
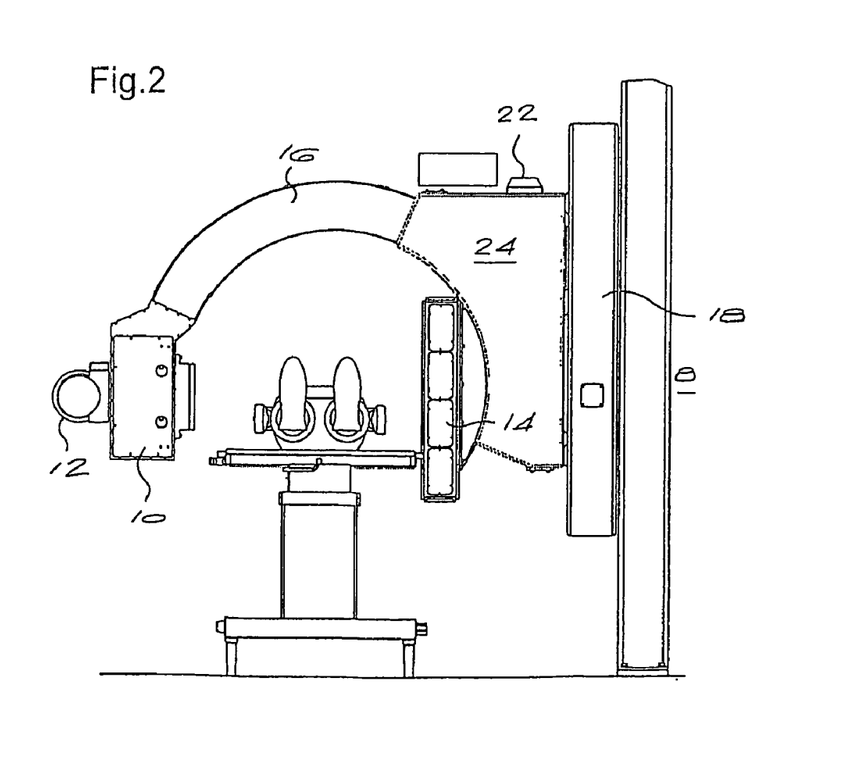
FIG. 2 is an end elevation of the apparatus of FIG. 1 showing a scanning arm thereof rotated through 90°.
Figure 3:
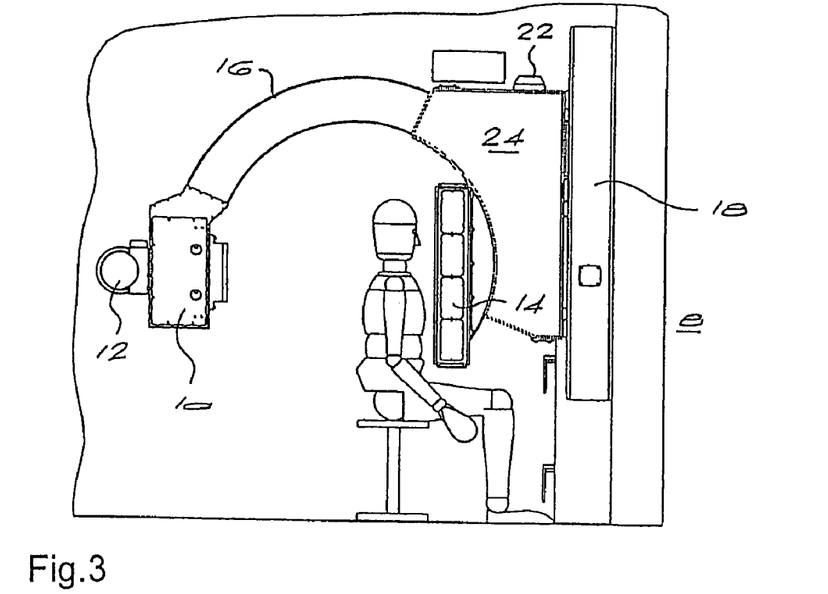
FIG. 3 is a similar view to that of FIG. 2, showing an alternative application of the apparatus.

FIGS. 1 to 3 show three different views of prototype X-ray imaging or scanning apparatus of the invention. The apparatus comprises a head 10 containing an X-ray source 12 which emits a narrow, fanned beam of X-rays towards a detector unit 14. The X-ray source 12 and the detector unit 14 are supported at opposite ends of a curved arm 16 which is generally semicircular or C-shaped.

A frame 18 mounted on a wall 8 or another fixed structure defines a pair of rails 20 with which a motorised drive mechanism 22 engages to drive the arm linearly back and forth in a first, axial direction of movement. This corresponds to the direction of scanning in use. In addition, the drive mechanism comprises a housing 24 in which the arm 16 is movable by the drive mechanism in order to cause the X-ray source and the detector to rotate about an axis parallel with the scanning direction of the mechanism.

Figure 4:
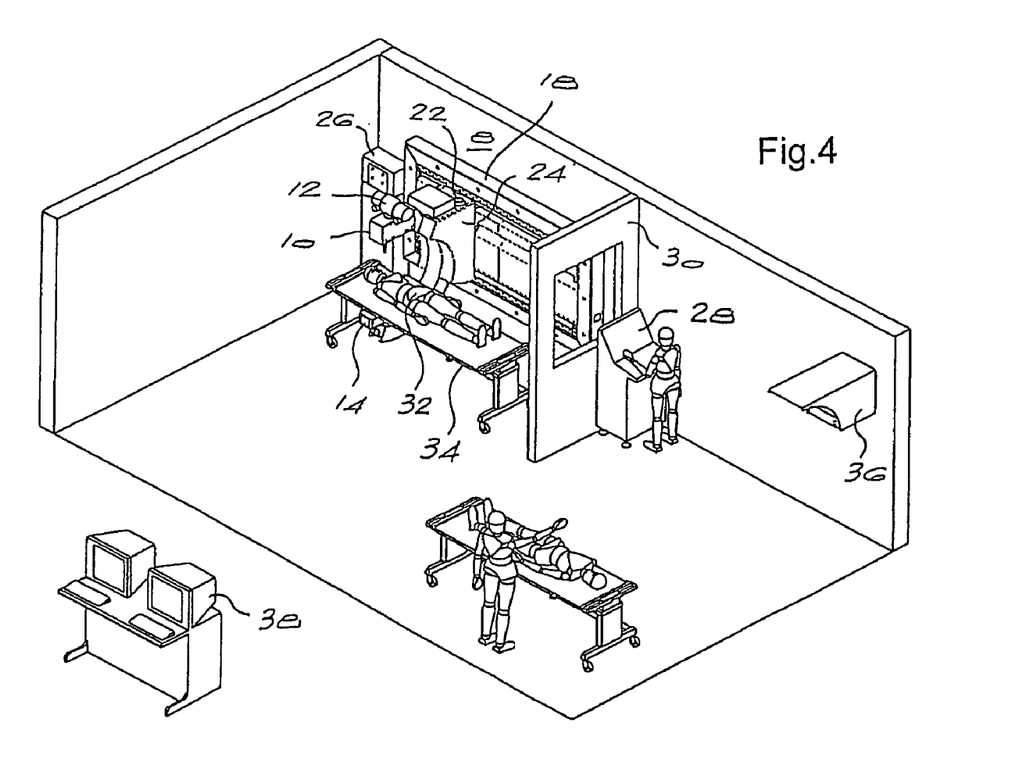
FIG. 4 is a pictorial view of a radiological installation incorporating the apparatus of the invention.

A typical application of the imaging apparatus of the invention is in a radiological installation, such as that illustrated in FIG. 4. The imaging apparatus is shown located in a corner of a room which may be a resuscitation area or trauma room of a hospital, for example. Alternatively, the apparatus may be located in a radiological department of a hospital or elsewhere.

Located adjacent to the imaging apparatus is a local positioning console 26, by means of which an operator can set up the required viewing parameters (for example, the angle of the arm 16, start and stop positions, and the width of the area to be X-rayed). A main operator console 28 is provided behind a screen 30 which is used by the operator to set up the required radiographic procedure. The imaging apparatus is operated to perform a scan of a subject 32 supported on a specialised trolley or gurney 34 (see below) and an image of the radiograph is displayed on a screen at the console 28, in order to allow the operator to judge whether a successful image has been acquired.

One or more high quality monitors 36 are provided for diagnostic viewing and are located so that attending clinical staff can study the radiographs being acquired. In addition, a console 38 is provided which forms part of a standard Radiological Information System which permits picture viewing and archiving.

The arrangement of FIG. 4 is designed for use in the resuscitation room of a trauma unit, in order to provide fast X-ray images of injured patients. Once a patient has been stabilised, he or she can conveniently be placed in position, scanned, and wheeled out for further treatment, with the resulting radiograph appearing on the diagnostic screen virtually instantaneously. Due to the low X-ray dose administered by the apparatus, the risk of radiation exposure to staff and patients is reduced.

The apparatus described above is generally similar to that described in International patent application no. WO 00/53093, the contents of which are incorporated herein by reference.

The X-ray source (tube) 12 emits a low-dose collimated fan-beam of X-rays. The X-ray detector unit 14 fixed to the other end of the C-arm 16 comprises a set of scintillator arrays optically linked to respective charge-coupled devices (CCDs). An image is acquired by linearly scanning the C-arm over the length of the subject (patient) 32 with the X-ray source active, whilst continuously reading the outputs of the detector unit in a mode analogous to "scrolling", thus building up a composite image.

In a prototype system of the invention, the individual pixels of the detector unit have a 60-micron size, providing up to 11600 elements along the length of the detector. This defines the width of the area to be scanned. Spatial resolutions of 1.04, 1.67, 2.78 or 4.17 line pairs per millimeter (lp/mm) are selectable. The system can record 14 bits of contrast resolution (>16000 grey scales) which compares favorably to the typically 1000 grey scales that can be detected on a conventional x-ray film under ideal viewing conditions. The C-arm is able to rotate axially around the patient to any angle up to 90 degrees, permitting horizontal-beam, shoot-through lateral, erect and oblique views.

The C-arm travels at speeds of up to 144 mm per second. The device is thus able to rapidly acquire images of part or all of the body of a patient, with a full body scan requiring 13 seconds, and with smaller areas requiring proportionately less time.

As indicated above, the system makes use of the technological principle sometimes referred to as "slit (or slot) scanning" and in this case, specifically "linear slit scanning". The detector is based on CCD technology running in the so-called "drift scanning", alternatively "TDI" (time-division integration) mode.

The X-rays emitted by the source 12 are highly collimated by a single slit that irradiates the detector with a narrow "fan beam" of x-rays. The fan beam is "narrow" (3 mm-6 mm) in the scanning direction and "wide" (~696 mm) in a direction transverse to the scanning direction.

If the fundamental pixel size at the detector front (X-ray detecting) face were 60 µm, then, according to the well known formula:

$$\text{Spatial resolution} = 1/(2 \times \text{pixel-size}) \text{ lp/mm}$$

a fundamental spatial resolution of 8.33 lp/mm would be obtained.

By combining (binning) the fundamental pixels into super pixels larger effective pixels are created. For example, super pixels could be formed by adding the output signals from orthogonal sets of adjoining fundamental pixels. Typical examples would be:

| | System "mode" designation: | | | |
|---|---|---|---|---|
| | Very High | High | Standard | Base |
| Array dimension of fundamental pixels | 2 × 2 | 3 × 3 | 5 × 5 | 8 × 8 |
| Spatial resolution (lp/mm) | 4.17 | 2.78 | 1.67 | 1.04 |
| Relative SNR per super pixel | 2 | 3 | 5 | 8 |

Note that for a fixed signal (i.e. X-ray flux) per unit area to be detected, the smaller the area resolved (i.e. size of effective pixel), the higher the spatial resolution that will be obtained. However, the smaller the area resolved (i.e. size of super pixel), the lower the SNR (signal to noise ratio) that could be obtained. The SNR directly affects the contrast resolution (ability to see small differences in grey scales) of the system. Thus, bigger pixels per unit input signal yield a better contrast resolution.

There are several other factors that impact on the spatial resolution of the whole system. Of relevance here is the geometric characteristics of the X-ray fan beam.

X-rays attempt to radiate isotropically from the so-called "target" or "spot size" inside the X-ray tube. In order to absorb the energy from the electron beam that impacts the target to generate the X-rays, the target has to be of a finite size. For an equivalent system, the more X-radiation generated, the bigger the target needs to be.

In the wide dimension, parallel to the slit, the degree of defocusing of images radiated by the X-ray beam is determined by the target size in the X-ray tube. In practice, this has a minimal effect on the spatial resolution within the practical limits of the system. However, in the scanning direction, corresponding to the narrow dimension of the X-ray fan beam, a different picture emerges, as illustrated schematically in FIG. 5.

Figure 5:
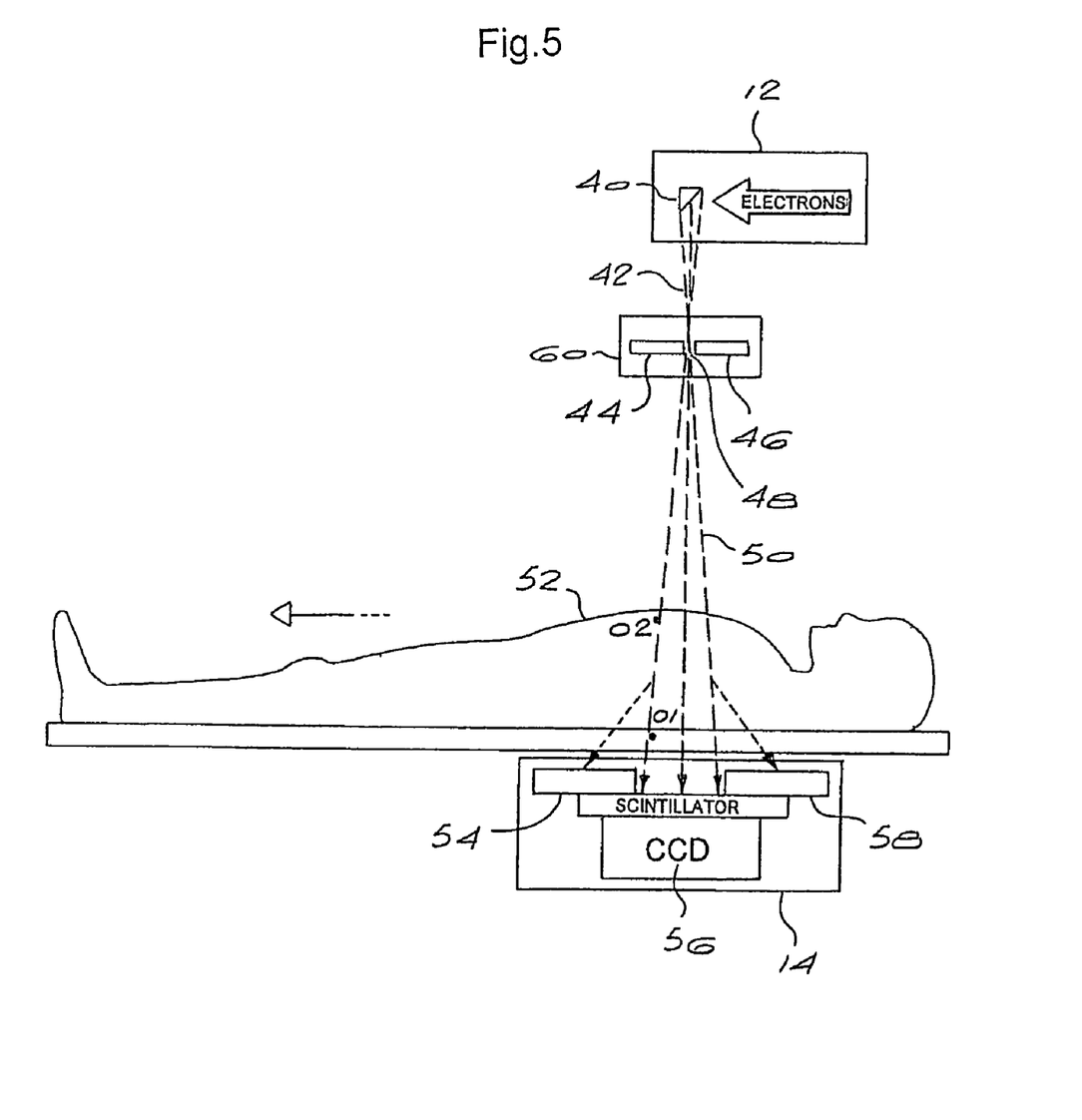
FIG. 5 is a schematic diagram illustrating the basic principles of operation of the imaging apparatus of the invention.

In FIG. 5, electrons in the X-ray tube 12 strike a target 40, which emits a beam of X-rays 42. The beam 42 is passed through a collimator comprising a pair of shutter elements 44 and 46 arranged side by side to define a narrow slit 48, and emerges as a narrow fan beam 50 as described above. The beam 50 passes through a patient 52 or other subject and strikes scintillator elements 54 mounted adjacent respective CCDs 56 in the detector unit 14. Anti-scatter strips 58 on either side of the detector unit absorb stray X-rays.

If one assumes that the target 40 is a point source then the X-ray fan beam 50 has the shape of an isosceles triangle in cross section, in the scanning direction. The base of the triangle (i.e. the beam width on the face of the detector unit 14) is determined by the width of the slit 48 in the main collimator. In the actual geometry used the base of the triangle varies from ~3 mm to 6 mm for a slit width of 0.6 mm to 1.2 mm, and for the sake of the following the actual target size can be ignored.

In order to make maximum possible use of the available X-ray power it is desirable to open the slit as much as possible. However this causes the X-ray beam to diverge further in the scanning direction. This has an undesirable side effect because it causes an effective de-focusing of the objects imaged. This can be described as an "error of parallax". See for example objects O1 and O2 in FIG. 5. Assume that they are directly in line with one another on a line at 90 degrees to the table top and that the X-ray fan beam is scanned from right to left in the direction of the arrow O1 will be registered on the detector before O2. Similarly as the back edge of the beam passes the objects, O2 will leave the field of view first. It is therefore evident that due to the divergence of the fan beam, objects in the field of view will "de-focus" in the direction of scanning.

It can therefore be seen that there is an inverse relationship between the width of the slit (and hence the width of the fan beam on the detector) and the spatial resolution of images that have depth, i.e. are not flat in the dimension between the X-ray target and the detector.

Therefore in a practical design the width of the slit opening is chosen to be as wide as possible, but so as to not degrade the desired spatial resolution in the scanning direction significantly.

Practical commercial x-generation systems (i.e. X-ray tube and generator combinations) increase rapidly in cost and also their availability decreases as the required X-ray output flux increases. Additionally, the higher heat load at higher powers causes undesirable operational delays while waiting for the system to cool down between X-ray procedures.

It is therefore highly desirable to use the minimum X-ray generation capacity in order to get the desired image quality for any X-ray procedure.

It is accepted practice in radiology that, inter-alia, various combinations of spatial and contrast resolution are used in order to gain ideal radiographs of various categories of patients and X-raying procedures. Examples of different categories include:

a. Mammography
b. Extremities
c. Chest
d. Lateral spine

Additionally, compromises from the ideal have to be used to ensure that diagnosable X-rays are obtained. Take for instance, example d, above: It is well known that obtaining good lateral X-rays of the spine, particularly of the cervical-thoracic junction, is extremely challenging. This is particularly so because of need to penetrate the patient's shoulders. The main focus in diagnosing these procedures is to be able to see the alignment of the spinal column, i.e. to see the positions of the vertebrae in relation to each other. The "noise" created by extraneous body parts as well as the scattering of X-rays whilst penetrating the lateral body through the shoulders, result in a poor signal to noise ratio that radically reduces the effective spatial and contrast resolution observable on the image. Therefore the X-ray dose is commonly pushed up very high when doing these procedures. Even then, the observable image quality is often barely good enough to just observe the alignment of the vertebrae. This problem is compounded when X-rays of larger patients have to be obtained.

To address this problem, the present invention proposes utilising a system with a variable slit width in the main collimator to vary the width of the X-ray beam in the scanning direction, thus increasing the effective X-ray dose and hence contrast resolution, but not at the expense of reducing the observable spatial resolution to below that which is commonly observable in equivalent conventional X-rays for equivalent procedures.

The use of the variable slit width can be combined with a technique of changing the effective pixel size to match the best spatial resolution expected at various slit width openings. With larger slit width openings, using bigger pixels would not generate a further degradation of the spatial resolution but would yield a significant increase in the contrast resolution, thus making the desired pathology much more observable.

Adjustment of the slit width and effective pixel size are done automatically in software by the system according to the patient size and X-ray procedure selected by the operator.

Figure 8:
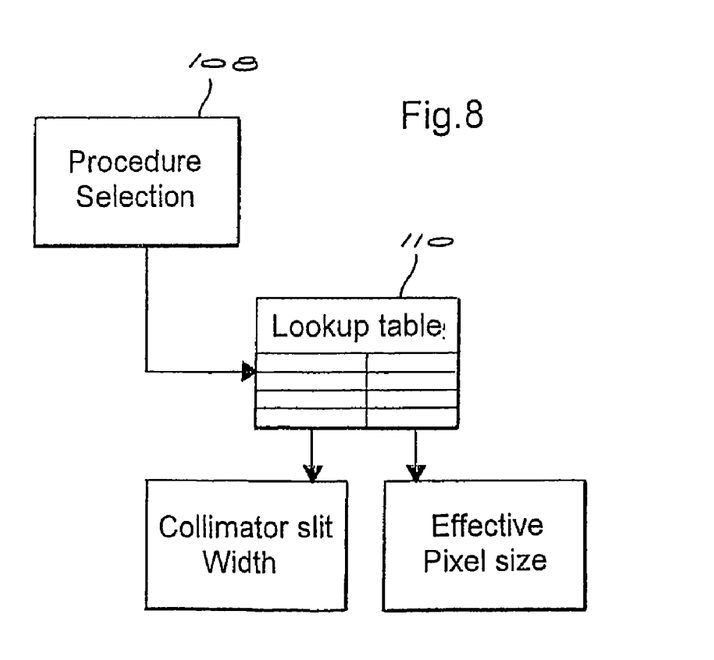
FIG. 8 is a highly simplified diagram indicating the relationship between collimator slit width and pixel size as utilized by the control circuit.

FIG. 8 shows, in a simplified diagrammatic form, how an operator procedure 108 automatically calls up suitable predetermined related values for collimator slit width and pixel size from a lookup table 110 when a value for patient size is selected from one of two or more patient size options.

A further scanning parameter that is of significance is the actual X-ray exposure time. In conventional full-field radiology, AEC (automatic exposure control) is commonly used. A method commonly used by X-ray generator manufacturers is for the system to automatically increase or reduce the time of the exposure according to the amount of signal measured once the X-rays have passed through the patient. This is intended to result in more optimum X-ray exposure in order to obtain the desired clarity on the image receptor.

However, this practice would not work in a conventional slit scanning system because the effective exposure time per unit object scanned is not proportional to the time set by the X-ray generator.

With the variable slit opening provided by the system of the present invention, the same effect may be achieved by adjusting the width of the slit continuously according the amount of X-ray signal that reaches the detector. In practice, the signal for each full detector line scanned is read and the slit width is continuously adjusted for the desired minimum signal level according to the lowest signal measured across the line scan width. This effectively provides automatic exposure control in a slit or slot scanning system. (See description below with reference to FIG. 7.)

Figure 6:
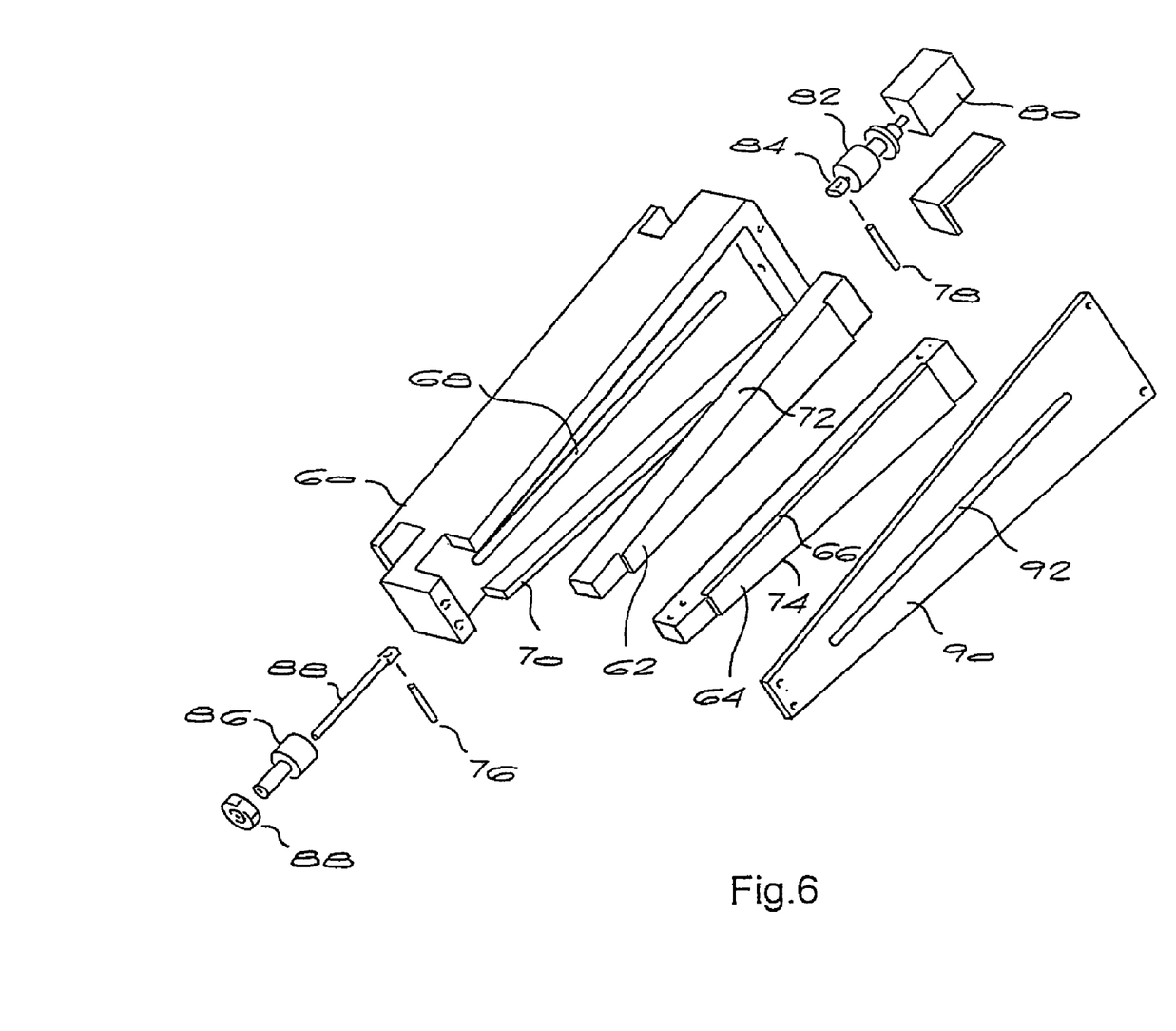
FIG. 6 is an exploded schematic view of a continuously adjustable collimator forming part of the apparatus.

FIG. 6 shows the adjustable collimator that is the heart of the present invention in a schematic, exploded view. The collimator comprises a housing 60 which receives a pair of tapered shutter elements 62 and 64. Each shutter element comprises a thin tungsten strip (typically 2 millimeters thick) mounted on a tapered supporting body. The interior of the housing 60 has tapered side walls 68 and 70 against which the tapered sides 72 and 74 of the shutter elements can slide smoothly. The angles of the side walls 68 and 70 and the tapered sides 72 and 74 of the shutter elements are matched, so that the tungsten strips 66 of the shutter elements remain parallel when the shutter elements are slid axially in the housing.

A pair of guide pins 76 and 78 are located in respective aligned apertures at opposite ends of the shutter elements, to maintain them in alignment relative to one another, and compression springs (not shown) located around the pins between the shutter elements bias them apart.

A rotary drive 80 comprising an electrical motor and reduction drive is connected to a ball screw mechanism 82 which converts the rotary motion of the reduction drive shaft to axial motion of a clevis 84. The clevis 84 fits about the pin 78 so that operation of the rotary drive causes axial displacement of the shutter elements in the housing. At the other end of the housing, a guide bush 86 is provided in which a clevis 88 can slide axially. The clevis 88 fits about the pin 76 and helps to maintain alignment of the shutter elements in use. A lock nut 88 holds the bush 86 in place. A cover 90 with a slot 92 slightly larger than the maximum slit opening of the collimator seals the housing.

A third compression spring (not shown) placed around the clevis 84 biases the shutter elements 62 and 64 towards the narrow end of the housing 60, and is sufficiently powerful to override the force of the twin compression springs urging the shutter elements apart, so that in the event of a malfunction of the rotary drive, the axial compression spring acts as a failsafe device to force the slot setting of the collimator to a minimum value.

In operation, the motor of the rotary drive is driven in one direction or the other to move the shutter elements axially in the housing and thus to increase or decrease the spacing and thus the slot width between them. The housing 60 is symmetrical, as are the shutter elements, ensuring that the gap remains parallel and maintains a constant center line. The angle of taper of the housing and shutter elements is relatively small, typically, but not limited to, 3 to 5 degrees so that minute changes in gap size can be achieved repeatedly, and symmetrically with reference to the centerline.

Instead of a rotary drive, a linear drive such as a solenoid could be used. In either case, the pins 76 and 78 set maximum and minimum gap limits. In the case of a solenoid drive, a simple two step adjustment will be available, which may be sufficient for some purposes. Alternatively, an additional solenoid can be fitted to provide a three position adjustment, for example.

On the opposite longitudinal end of the collimator housing is the facility to mount a position feedback control unit, in the form of a limit switch or a rotary or linear position sensor, for example.

Figure 7:
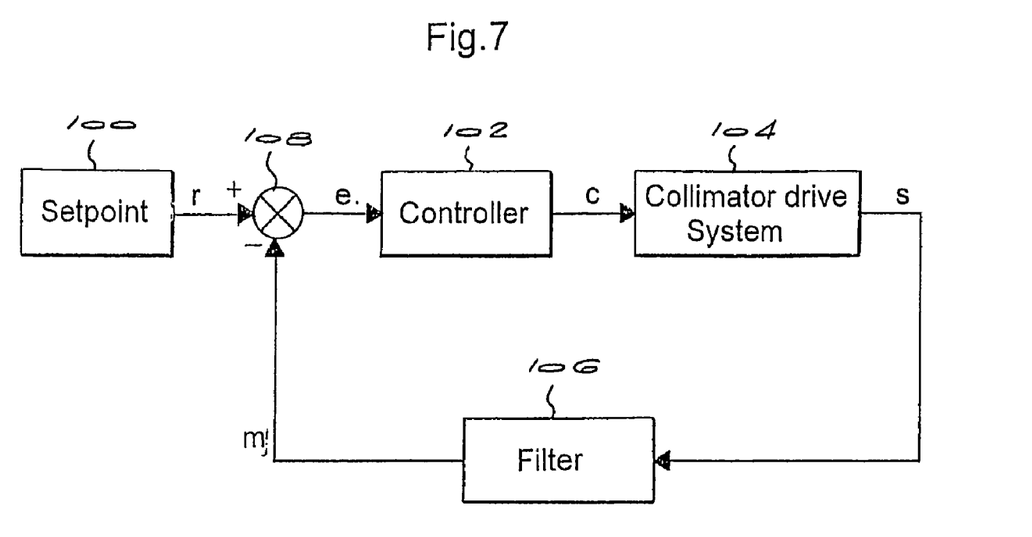
FIG. 7 is a highly simplified schematic block diagram of a control circuit of the apparatus.

FIG. 7 shows the arrangement, in a highly schematic block diagram, of a controller for implementing the above described AEC function. A setpoint controller 100 is adjusted to specify a desired minimum average detected signal level r. A controller 102 calculates a control signal c which is derived from an error signal e. The control signal c is fed to a collimator drive system 104, which operates the drive of the variable slit collimator and generates an output s corresponding to a detected scanline (i.e. the signal level of the detected imaging beam once it has passed through the subject). This output is fed to a filter 106 which generates a scalar output value m, which is the minimum average value of the scanline signal level. The value m is fed to a comparator 108 which compares the value of m with the setpoint r to generate the error signal e. Thus, the controller operates to adjust the collimator slit width to maintain the value of m as close as possible to the setpoint value r.

In an experimental prototype of the invention, images of a test subject were acquired with and without the addition of a 200 mm water phantom (flat rectangular water filled container) with identical X-ray parameters. With a standard setting of the apparatus, the cervical-thoracic vertebrae of the subject were clearly visible. With the water phantom in place, simulating a large patient, the relevant vertebrae were obscured. However, utilizing a larger slit width combined with larger effective pixel size, corresponding to an "Extra large patient procedure" setting of the apparatus, the alignment of the vertebrae again became clearly visible.

The invention claimed is:

1. Imaging apparatus comprising:
   a radiation source for generating an imaging beam;
   a detector responsive to the imaging beam to generate image signals and comprising an array of pixels arranged in rows and columns, each pixel being responsive to incident radiation to generate an output signal;
   a drive arranged to move the radiation source and the detector relative to a subject in a scanning direction;
   an adjustable collimator arranged to vary the width of the imaging beam in the scanning direction; and
   a control system responsive to adjustment of the collimator to combine the output signals of groups of pixels comprising greater numbers of pixels automatically as the collimator is adjusted to increase the width of the imaging beam in the scanning direction, thereby to increase the contrast resolution of the image signals for a given spatial resolution.

2. Apparatus according to claim 1 wherein each group of pixels defines a super pixel comprising an array of fundamental pixels, the number of fundamental pixels in the array being selected according to a corresponding collimator setting.

3. Apparatus according to claim 2 wherein the relationship between collimator settings and the number of fundamental pixels in an array defining a super pixel is stored in a lookup table and related to respective ones of a plurality of different x-ray procedures.

4. Apparatus according to claim 1 wherein the control system is arranged to measure the signal level of the detected imaging beam and to adjust the collimator slit width to maintain the detected signal level at or close to a desired setpoint.

5. A method of operating imaging apparatus of the kind having a radiation source and an associated detector which are moveable relative to a subject, the method comprising:
generating an imaging beam from the radiation source;
moving the radiation source and the detector relative to a subject in a scanning direction to generate output signals from each of a plurality of pixels of the detector;
adjusting a collimator to vary the width of the imaging beam in the scanning direction;
detecting the setting of the collimator; and
combining the output signals of groups of two or more pixels according to the setting of the collimator, thereby to optimize a selected characteristic of the image signals.

6. A method according to claim 5 comprising combining the output signals of groups of pixels comprising greater numbers of pixels as the collimator is adjusted to increase the width of the imaging beam in the scanning direction, thereby to increase the contrast resolution of the image signals for a given spatial resolution.

7. A method according to claim 5 wherein each group of pixels defines a super pixel comprising an array of fundamental pixels, the number of fundamental pixels in the array being selected according to a corresponding collimator setting.

8. A method according to claim 5 wherein the relationship between collimator settings and the number of fundamental pixels in an array defining a super pixel is stored in a lookup table and related to respective ones of a plurality of different x-ray procedures.

9. A method according claim 5 including measuring the signal level of the detected imaging beam and adjusting the collimator slit width to maintain the detected signal level at or close to a desired setpoint.

10. A collimator for adjusting the effective width of an imaging beam generated by a radiation source, the collimator comprising:

first and second shutter elements arranged side by side and including respective first and second tapered surfaces, and further including respective first and second slit-forming surfaces forming therebetween a slit through which radiation emitted by the source can pass, the slit having a length and a width of shorter dimension than the length, the width defined by a distance between the slit-forming surfaces;
a guide mechanism comprising first and second tapered surfaces arranged to cooperate with respective ones of the first and second tapered surfaces on the first and second shutter elements; and
a drive mechanism arranged to produce first sliding movement between the first tapered surface of the first shutter element and the first tapered surface of the guide mechanism, and second sliding movement between the second tapered surface of the second shutter element and the second tapered surface of the guide mechanism, to cause the first and second slit-forming surfaces to move relative to one another in the direction of the slit's width to vary the dimension of that width.

11. A collimator according to claim 10 wherein the imaging beam is directed towards a detector, the drive mechanism comprising a single motor that produces both of the first and second sliding movements, wherein both of the shutter elements are arranged to move co-centrically with respect to a centre line that passes through the slit along the slit's length, to obtain an optimum umbra to penumbra ratio of the imaging beam on the detector.

12. A collimator according to claim 10 wherein each shutter element comprises a strip of radiation-opaque material defining the respective slit-forming surface, and a supporting body carrying the respective strip and defining the respective tapered surface.

13. A collimator according to claim 10 wherein the drive mechanism comprises a motor, a reduction drive connected to the motor, and a mechanism connected to the reduction drive and arranged to impart linear motion to both shutter elements to effect the first and second sliding movements.

14. A collimator according claim 10 wherein the motor comprises a solenoid.

15. A collimator according claim 10 wherein the first and second tapered surfaces of the first and second shutter elements are biased towards one another, wherein the drive mechanism is operable to move those first and second tapered surfaces away from one another against the bias.

* * * * *